US009687148B2

(12) United States Patent
Makihira

(10) Patent No.: US 9,687,148 B2
(45) Date of Patent: Jun. 27, 2017

(54) PHOTOGRAPHING APPARATUS AND PHOTOGRAPHING METHOD

(71) Applicant: CANON KABUSHIKI KAISHA, Tokyo (JP)

(72) Inventor: Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 6 days.

(21) Appl. No.: 14/631,880

(22) Filed: Feb. 26, 2015

(65) Prior Publication Data

US 2015/0173612 A1 Jun. 25, 2015

Related U.S. Application Data

(62) Division of application No. 13/400,990, filed on Feb. 21, 2012, now Pat. No. 8,992,018.

(30) Foreign Application Priority Data

Mar. 10, 2011 (JP) .................................. 2011-052290

(51) Int. Cl.
*A61B 3/12* (2006.01)
*A61B 3/14* (2006.01)
(Continued)

(52) U.S. Cl.
CPC ................ *A61B 3/12* (2013.01); *A61B 3/102* (2013.01); *A61B 3/1225* (2013.01); *A61B 3/14* (2013.01);
(Continued)

(58) Field of Classification Search
CPC .. A61B 3/12; A61B 3/10; A61B 3/102; A61B 3/1025; A61B 3/113; A61B 3/1225;
(Continued)

(56) References Cited

U.S. PATENT DOCUMENTS 6,325,512 B1 12/2001 Wei
7,510,282 B2 3/2009 Ueno et al.
(Continued)

FOREIGN PATENT DOCUMENTS

CN 102232824 A 11/2011
EP 1 882 445 A2 1/2008
(Continued)

OTHER PUBLICATIONS

Jun. 21, 2012 European Search Report in European Patent Appln. No. 12158358.7.
(Continued)

*Primary Examiner* — Jordan Schwartz
(74) *Attorney, Agent, or Firm* — Fitzpatrick, Cella, Harper & Scinto

(57) ABSTRACT

The present invention provides an ophthalmological apparatus capable of displaying a plurality of fundus tomographic images. A photographing apparatus includes a fundus imaging unit adapted to capture a fundus image of a subject's eye, a scanning unit adapted to scan a desired position of the fundus of the subject's eye to capture tomographic images of the subject's eye, a measuring unit adapted to measure movement amounts of the fundus of the subject's eye by performing pattern matching between a plurality of feature points in the acquired fundus image and feature points in another fundus image newly acquired at a different time, and a control unit adapted to control the scanning unit based on the measured movement amounts.

19 Claims, 10 Drawing Sheets

(51) Int. Cl.
*A61B 3/10* (2006.01)
*G01B 9/02* (2006.01)
*G01N 21/47* (2006.01)
*G06T 7/20* (2017.01)

(52) U.S. Cl.
CPC ..... *G01B 9/02091* (2013.01); *G01N 21/4795* (2013.01); *G06T 7/20* (2013.01); *G06T 2207/10101* (2013.01)

(58) Field of Classification Search
CPC ........ A61B 3/14; G01B 9/02091; G06T 7/20; G06T 2207/10101
See application file for complete search history.

(56) References Cited

U.S. PATENT DOCUMENTS

| | | | |
|---|---|---|---|
| 7,805,009 B2 | 9/2010 | Everett et al. | |
| 8,050,504 B2 | 11/2011 | Everett et al. | |
| 8,363,958 B2 | 1/2013 | Everett et al. | |
| 8,649,611 B2 | 2/2014 | Everett et al. | |
| 8,919,959 B2 | 12/2014 | Makihira | |
| 8,992,018 B2 * | 3/2015 | Makihira | A61B 3/102 351/206 |
| 2006/0228011 A1 | 10/2006 | Everett et al. | |
| 2008/0024721 A1 | 1/2008 | Ueno et al. | |
| 2008/0100612 A1 * | 5/2008 | Dastmalchi | G06F 19/321 345/418 |
| 2010/0182612 A1 * | 7/2010 | Yoshida | A61B 3/102 356/511 |
| 2010/0238403 A1 | 9/2010 | Kobayashi et al. | |
| 2010/0296056 A1 | 11/2010 | Uchida | |
| 2011/0234785 A1 | 9/2011 | Wanda et al. | |
| 2011/0267580 A1 | 11/2011 | Nakajima et al. | |
| 2011/0267581 A1 | 11/2011 | Nakajima et al. | |
| 2012/0002166 A1 | 1/2012 | Tomatsu et al. | |
| 2012/0033181 A1 * | 2/2012 | Koizumi | A61B 3/102 351/208 |
| 2012/0154747 A1 | 6/2012 | Makihira | |
| 2012/0229762 A1 | 9/2012 | Makihira | |
| 2012/0229763 A1 | 9/2012 | Suehira et al. | |
| 2012/0229764 A1 | 9/2012 | Tomatsu et al. | |
| 2012/0229765 A1 | 9/2012 | Makihira | |
| 2013/0222762 A1 | 8/2013 | Everett et al. | |

FOREIGN PATENT DOCUMENTS

| | | |
|---|---|---|
| EP | 2 382 913 A1 | 11/2011 |
| EP | 2 382 914 A1 | 11/2011 |
| JP | 2004-512125 A | 4/2004 |
| JP | 2004-159767 A | 6/2004 |
| JP | 2008-029467 A | 2/2008 |
| JP | 2010-012109 A | 1/2010 |
| WO | 2010/113459 A1 | 10/2010 |
| WO | WO 2010/119632 * | 10/2010 |

OTHER PUBLICATIONS

Feb. 24, 2014 Chinese Official Action in Chinese Patent Appln. No. 201210063802.8.

\* cited by examiner

PHOTOGRAPHING APPARATUS AND PHOTOGRAPHING METHOD

This application is a division Application No. 13/400,990 filed Feb. 21, 2012.

BACKGROUND OF THE INVENTION

Field of the Invention

The present invention relates to a photographing apparatus and photographing method. More particularly, the present invention relates to a photographing apparatus and photographing method which acquire desired fundus tomographic images by reflecting moving amounts of the fundus in tomographic fundus imaging in real time.

Description of the Related Art

Recently, OCT (Optical Coherence Tomography) apparatus capable of acquiring fundus tomographic images have been attracting attention. One of the contributing factors in attracting attention is the capability to noninvasively examine the internal structure of the fundus which cannot be observed with other apparatus. FD-OCT (Fourier Domain OCT) which has a proven track record in high-speed imaging serves the center of the market. The OCT apparatus incorporates a fundus camera and a SLO (Scanning Laser Ophthalmoscope) and thereby allows OCT images to be acquired around a desired location by displaying which area of the fundus to be OCT-scanned.

On the other hand, for the purposes of detection of minute tumors or abnormalities in early diagnosis and early treatment, there is demand for improvements in image quality of OCT images. To achieve high image quality, a technique related to an apparatus (National Publication of International Patent Application No. 2004-512125) which makes an OCT beam follow fundus movements, i.e., changes in fundus location resulting from eye ball movements has been disclosed.

Also, a technique for capturing SLO images and OCT images alternately is disclosed (Japanese Patent Application Laid-Open No. 2008-029467) in relation to the above-described OCT apparatus equipped with the SLO apparatus.

In the configuration disclosed in National Publication of International Patent Application No. 2004-512125, a device adapted to detect fundus movements is added to the OCT apparatus. The device acquires OCT images of a desired site by tracking the optic disk in the fundus and controlling an OCT scanner in real time.

Also, by capturing SLO images and OCT images alternately, the configuration disclosed in Japanese Patent Application Laid-Open No. 2008-029467 acquires the SLO images and OCT images while reducing the burden on the patient.

As a result of FD-OCT's speedup, it may take a shorter time to acquire OCT images than to acquire fundus movement information. This will be described with reference to FIG. 3. When the OCT beam O is moved to a desired location and measurements are started, a plurality of OCT images 311 to 322 is acquired while SLO images 301 to 304 are acquired to calculate positional information. In this case, there is a problem in that positional information corresponding to all the OCT images is not available.

High-speed tracking will solve the above problem as with the invention disclosed in National Publication of International Patent Application No. 2004-512125, but it becomes essential to add a special device dedicated to tracking, resulting in a size increase of the apparatus, and furthermore in the need for expensive parts such as a tracking scanner.

Also, there is a problem of increased initial operations such as setting of a target to be tracked, resulting in an increased imaging time.

Also, the invention disclosed in Japanese Patent Application Laid-Open No. 2008-029467 has a problem in that since SLO images and OCT images are acquired alternately, imaging takes much time, which can cause long delay times in the case of real-time tracking, resulting in a large deviation from the fundus location.

SUMMARY OF THE INVENTION

An object of the present invention is to allow real-time tracking to be performed appropriately even when an acquisition rate of fundus images is lower than an acquisition rate of tomographic images.

To solve the above problem, the present invention provides a photographing apparatus which measures movements of an eye to be inspected by matching using a plurality of characteristic images extracted from a fundus image of the eye to be inspected, and which comprises a tomographic image acquisition unit adapted to acquire a tomographic image of the eye to be inspected, the tomographic image acquisition unit including: a scanning unit adapted to scan measuring light to obtain the tomographic image; a fundus image acquisition unit adapted to acquire the fundus image of the eye to be inspected; a measuring unit adapted to measure the movements of the eye to be inspected, by executing matching using at least one of the plurality of characteristic images extracted from the fundus image acquired by the fundus image acquisition unit; and a control unit adapted to control the scanning unit in obtaining the tomographic image, based on the movements of the eye to be inspected, measured by the measuring unit by executing matching using at least one of the characteristic images, wherein the measuring unit performs the measurement during acquisition of the fundus image by the fundus image acquisition unit.

Also, the present invention provides a photographing method for measuring movements of an eye to be inspected, by pattern matching using a plurality of feature points extracted from a fundus image of the eye to be inspected, comprising: acquiring the fundus image of the eye to be inspected; measuring the movements of the eye to be inspected, by executing pattern matching using the plurality of feature points extracted from the fundus image acquired by the acquiring the fundus image of the eye to be inspected; capturing a tomographic image of the eye to be inspected, based on the movements of the eye to be inspected, measured by the measuring, wherein the capturing operates according to the movements measured by the measuring based on one of the feature point.

The present invention allows real-time tracking to be performed appropriately with a reduced delay time between position detection and position correction.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

First Embodiment

A first embodiment of the present invention will be described below.

According to the present embodiment, a fundus image is acquired using SLO, a plurality of feature points (also referred to as characteristic images) are extracted from the image (SLO image) acquired by SLO, and a moving amount of the fundus is measured each time a feature point is detected. Results are fed back to a scanner of an OCT apparatus in real time to acquire an OCT image and thereby control a scan area of an OCT beam to be at a desired position in the fundus. Description will be given of a configuration in which after the entire SLO image is acquired, relative rotation and magnification of the fundus image are calculated based on the plurality of feature points and the relative rotation and magnification of the fundus image are fed back to scanning of the OCT beam.

(Configuration of OCT Imaging Unit)

Figure 1:
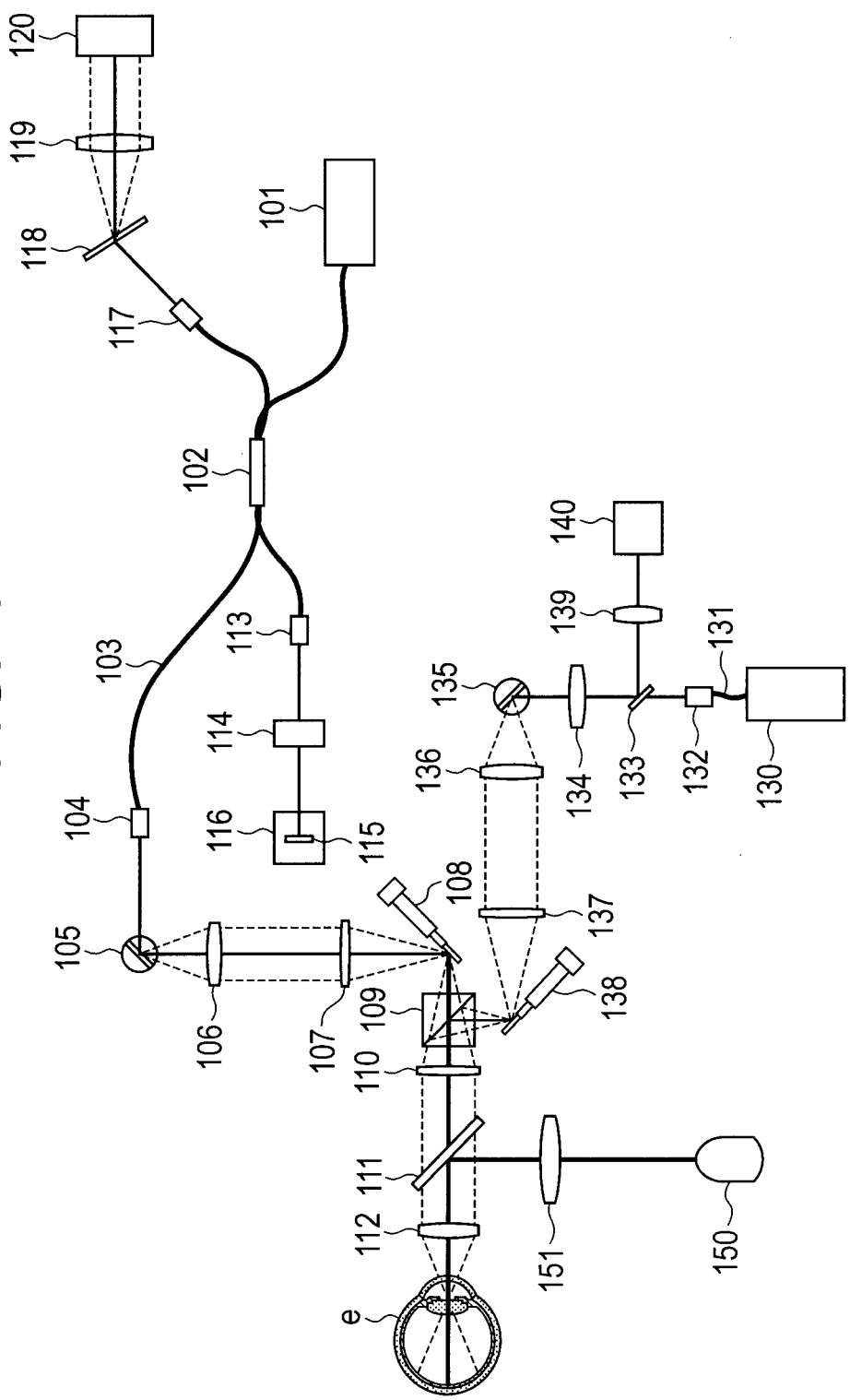
FIG. 1 is a schematic diagram of a function system of an apparatus according to a first embodiment of the present invention.

An optical configuration of an imaging unit serving as a tomographic image acquisition unit according to the present invention will be described with reference to FIG. 1.

Regarding a light source, a low-coherence light source 101 is used. As the light source 101, an SLD (Super Luminescent Diode) light source or ASE (Amplified Spontaneous Emission) light source can be used suitably. Regarding low-coherence light, wavelengths around 850 nm and 1050 nm are used suitably for fundus photography. An SLD light source with a center wavelength of 840 nm and a half-wavelength of 45 nm is used in the present embodiment. The low-coherence light emitted from the low-coherence light source 101 enters a fiber coupler 102 through fiber and is divided into measuring light (OCT beam) and reference light. An interferometer configuration using fiber is described herein, but a configuration using a beam splitter in a space optical system may be adopted alternatively.

The measuring light is emitted as parallel light from a fiber collimator 104 through a fiber 103. The parallel light passes through an OCT scanner (Y) 105, relay lenses 106 and 107, an OCT scanner (X) 108, a dichroic beam splitter 109, a scan lens 110, a dichroic mirror 111, and an eyepiece 112 and illuminates a subject's eye (eye to be inspected) e. Galvano scanners are used as the OCT scanner (X) 108 and OCT scanner (Y) 105 serving as a scanning unit according to the present invention. In the subject's eye e, the measuring light is reflected off the retina and returns to the fiber coupler 102 through the same optical path. The reference light is led from the fiber coupler 102 to a fiber collimator 113 and emitted therefrom as parallel light. The emitted reference light is passed through dispersion correction glass 114 and reflected by a reference mirror 116 on a stage 115 whose optical path length is variable. The reference light reflected by the reference mirror 116 returns to the fiber coupler 102 through the same optical path.

The fiber coupler 102 combines the returning measuring light and reference light and the resulting light is led to a fiber collimator 117. The combined light is referred to herein as interfering light. The fiber collimator 117 makes up a spectroscope in conjunction with a transmission grating 118, a lens 119 and a line sensor 120. The interfering light is measured as intensity information at each wavelength by the spectroscope. The wavelength-specific intensity information measured by the line sensor 120 is transferred to a PC (not shown) to generate a tomographic image of the subject's eye e.

(Configuration of SLO Imaging Unit)

Next, an optical configuration of an SLO imaging unit will be described also with reference to FIG. 1, where the SLO imaging unit acquires fundus images by serving as a fundus image acquisition unit according to the present invention. As a laser light source 130, a semiconductor laser or SLD light source is used suitably. There are no constraints on usable wavelengths as long as the usable wavelengths can be separated from each other by the wavelength of the low-coherence light source 101 of the OCT imaging unit and the dichroic beam splitter 109, but the near-infrared wavelength region from 700 nm to 1000 nm is used suitably when image quality of fundus observation is taken into consideration. A semiconductor laser with a wavelength of 760 nm is used in the present embodiment. A laser (SLO beam) emitted from the laser light source 130 is passed through a fiber 131, emitted as parallel light from a fiber collimator 132, and led to an SLO scanner (Y) 135 through a perforated mirror (ring mirror) 133 and a lens 134. Then, after passing through lenses 136 and 137 and a SLO scanner (X) 138 and being reflected by the dichroic beam splitter 109, the SLO beam enters the subject's eye e. The dichroic beam splitter 109 is configured to transmit OCT beams and reflect SLO beams. As with the OCT imaging unit, galvano scanners are used as the scanners of the SLO imaging unit. The SLO beam incident upon the subject's eye e illuminates the fundus of the subject's eye e. The beam is reflected or scattered by the fundus of the subject's eye e and returns to the ring mirror 133 through the same optical path. Position of the ring mirror 133 is conjugate to pupil position of the subject's eye e. Consequently, when the beam illuminating the fundus backscatters, rays passing through the periphery of the pupil are reflected by the annular mirror 133 and focused onto an APD (avalanche photodiode) 140 by a lens 139. Based on intensity information from the APD 140, the PC (not shown) generates a planar image (fundus image) of the fundus.

(Internal Fixation Lamp)

According to the present embodiment, to enable stable fixation, an internal fixation lamp to fix the subject's eye e on is provided. The internal fixation lamp will be described with reference to FIG. 1 as in the case of the OCT imaging unit and SLO imaging unit. The internal fixation lamp 150 used herein is made up of a plurality of light-emitting diodes (LDs) arranged in a matrix. Lighting position of the light-emitting diodes is changed according to a desired imaging region under the control of the PC. The light-emitting diodes have a wavelength of 500 nm. A beam emitted from the internal fixation lamp 150 illuminates the subject's eye e by passing through a lens 151 and the dichroic mirror 111. Consequently, a tomographic image can be captured at a desired position by making the subject's eye e gaze at the beam. The dichroic mirror 111 is located between the scan lens 110 and eyepiece 112 and adapted to separate the wavelength of the fixation light (about 500 nm) from the wavelengths of the OCT beam and SLO beam (700 nm or above).

(Unit Configuration and Control)

Figure 2:
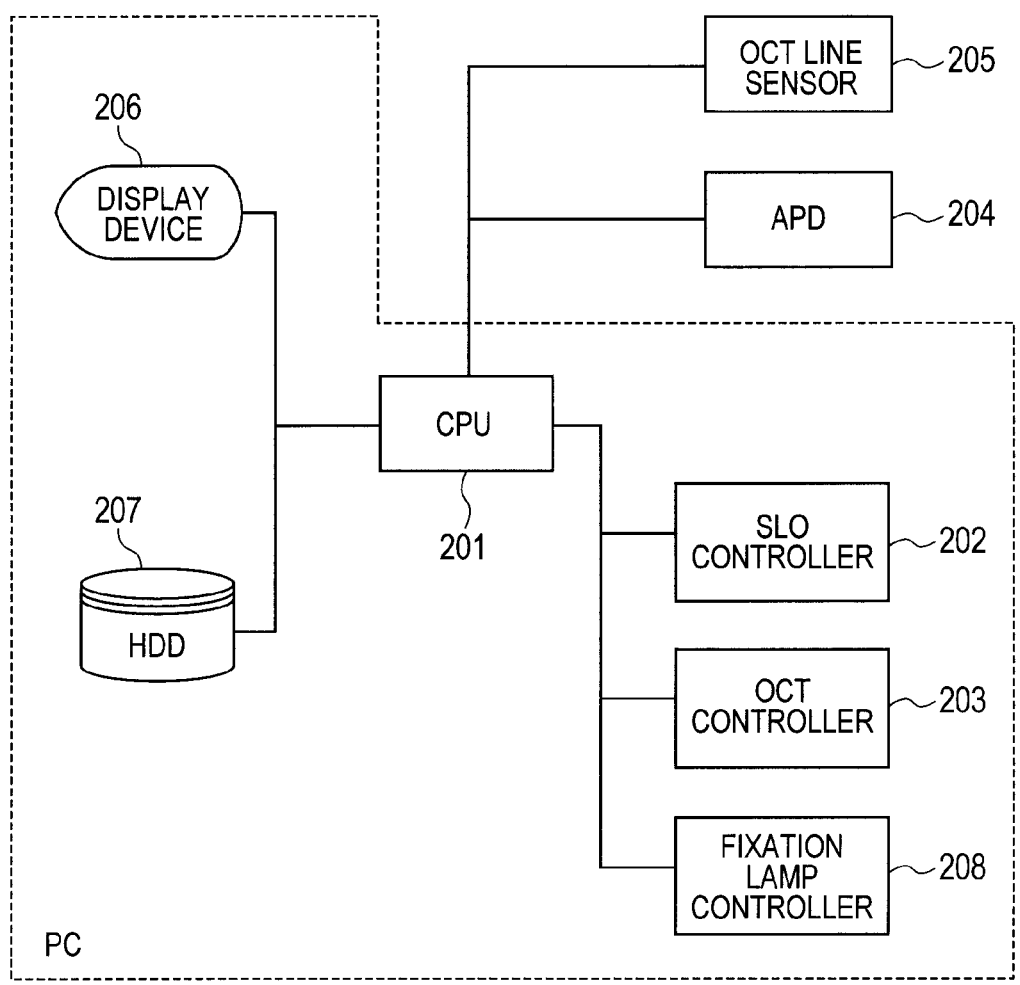
FIG. 2 is a schematic diagram of an ophthalmological apparatus according to the first embodiment of the present invention.

A function system used in the present embodiment is shown in FIG. 2. The function system includes a CPU 201 adapted to control the entire system; controllers 202 and 203 adapted to respectively control the SLO imaging unit and OCT imaging unit which are main components; a fixation lamp controller 208; an APD 204 (140) and line sensor 205 (120) adapted to acquire SLO images and OCT images, respectively; a display device 206 adapted to display system states; and a recording unit 207 adapted to record fundus images, imaging conditions, and the like. During fundus imaging, the fixation lamp controller 208 controls the lighting position of the internal fixation lamp 150, on which the subject's eye is then caused to be fixed, the CPU 201 specifies imaging conditions to the controllers 202 and 203, the scanners are driven, and the fundus is imaged. After the fundus is imaged, images are sent from the APD 204 and line sensor 205 to the CPU 201, subjected to image processing (to generate an SLO image and OCT image), displayed on the display unit 206, and simultaneously or subsequently saved in the recording unit 207.

(Tracking Control)

Figure 8:
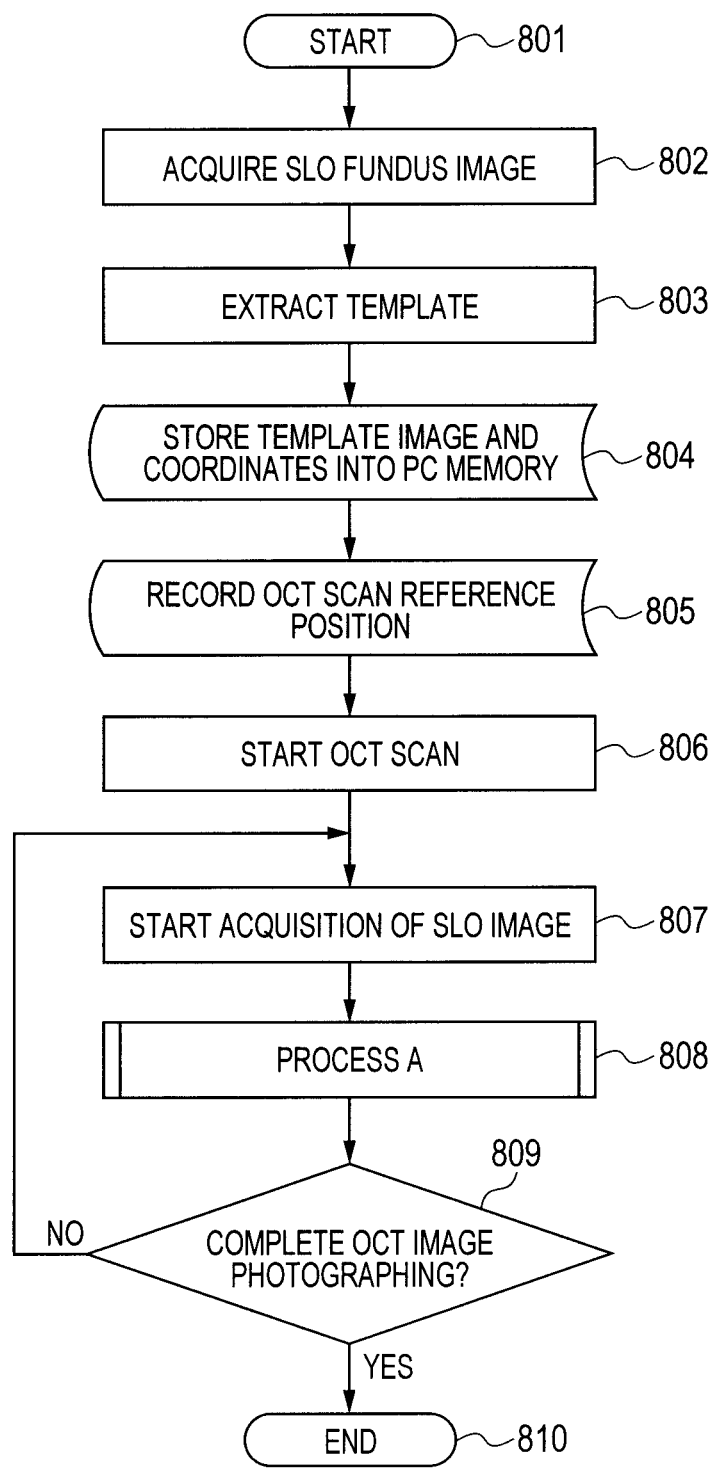
FIG. 8 is a schematic diagram of a processing flow according to the first embodiment of the present invention.

Using the apparatus described above, movement amounts of the fundus of the subject's eye are calculated from the SLO image and fed back to the X and Y scanners of the OCT imaging unit. While the fundus of the subject's eye is being monitored, a fundus image of the patient is acquired using the SLO imaging unit and a plurality of feature points is extracted from the fundus image and recorded in the recording unit. After the feature points are extracted and recorded, it is checked whether an SLO image being newly acquired contains any feature point already recorded. If any such feature point is detected, X and Y shift amounts are calculated from coordinates of the extracted feature point and detected feature point. After the shift amounts are calculated, voltages to be applied to the scanners of the OCT imaging unit are determined from the calculated values and the X and Y galvano scanners 108 and 105 of the OCT imaging unit are driven. The above processes will be described with reference to a flowchart in FIG. 8. First, in a fundus image acquisition step of acquiring a fundus image, a fundus image is acquired by the SLO apparatus (step 802). Feature points (hereinafter referred to as templates) are extracted from the acquired SLO image (step 803). The extracted template images and their coordinates are saved in PC memory (step 804). A scan reference position of the OCT apparatus is recorded (step 805). OCT imaging is started (step 806). An SLO image is acquired at the same time (step 807). In process A, a moving amount of the fundus is fed back to the OCT scanners and real-time tracking is performed (step 808). Steps 807 to 809 described above are repeated until the OCT imaging is completed. The above steps are carried out under the control of the CPU 201 (FIG. 2).

Figure 9:
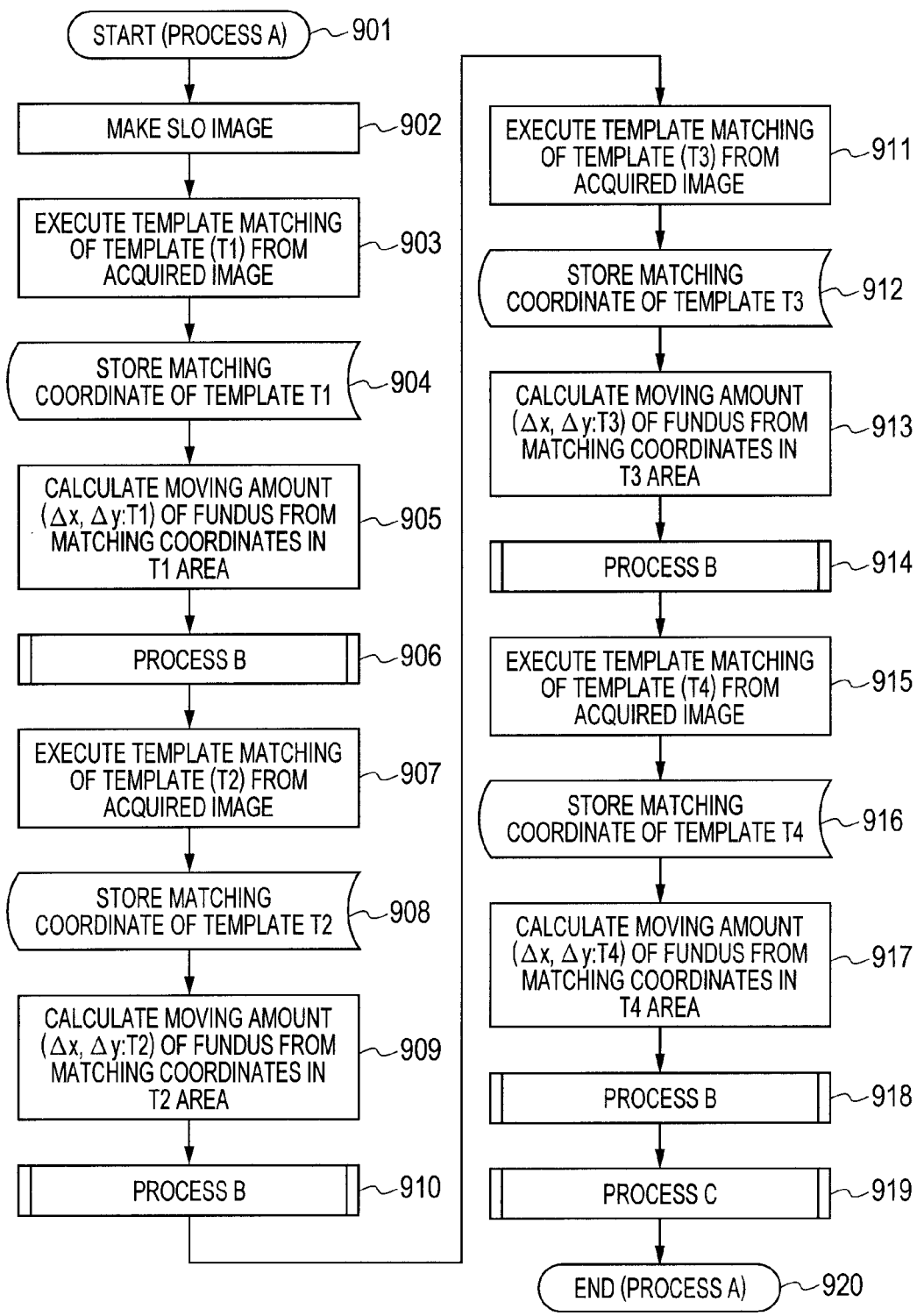
FIG. 9 is a schematic diagram of process A according to the first embodiment of the present invention.

Process A will be described with reference to FIG. 9. While a fundus image is being constructed from an SLO signal (step 902), an image of an ith template which corresponds to a template T1 is searched for and pattern matching is executed (step 903). The coordinates of the matching template are saved (step 904). A moving amount ($\Delta x$, $\Delta y$) of the fundus is calculated based on the coordinates of the matching template and coordinates of the extracted template image (step 905). These steps correspond to a measuring step according to the present invention, where the measuring step involves measuring the movements of the subject's eye by executing pattern matching using a plurality of feature points extracted from the acquired fundus image. Also, these operations are performed by that section of the CPU 201 which functions as a measuring unit adapted to select one of the plurality of feature points extracted from the acquired fundus image and measure the movements of the subject's eye by executing pattern matching using the selected feature point. Incidentally, the matching operation is not limited to those which use so-called image patterns, and thus preferably the operation is referred to as matching. In process B, the calculated moving amount of the fundus is fed back to the X and Y galvano scanners 108 and 105 of the OCT imaging unit (step 906). The above processes are also performed for T2 to T4 (steps 907 to 910, steps 911 to 914, and steps 915 to 918). In process C, after information on all the templates T1 to T4 of the fundus image is obtained, recalculation is performed to calculate rotation and magnification changes of the fundus based on the coordinates and moving amounts of T1 to T4 (step 919). In performing the recalculation, preferably at least one feature point, and more preferably two or more feature points are extracted or specified. The scanning unit adapted to obtain a tomographic image based on the movements of the subject's eye thus measured by the measuring unit is controlled by that section of the CPU 201 which functions as a control unit. Also, when the movements of the subject's eye are measured based on the extracted or specified feature points, preferably measurements are taken in the order in which the feature points are extracted.

Figure 10:
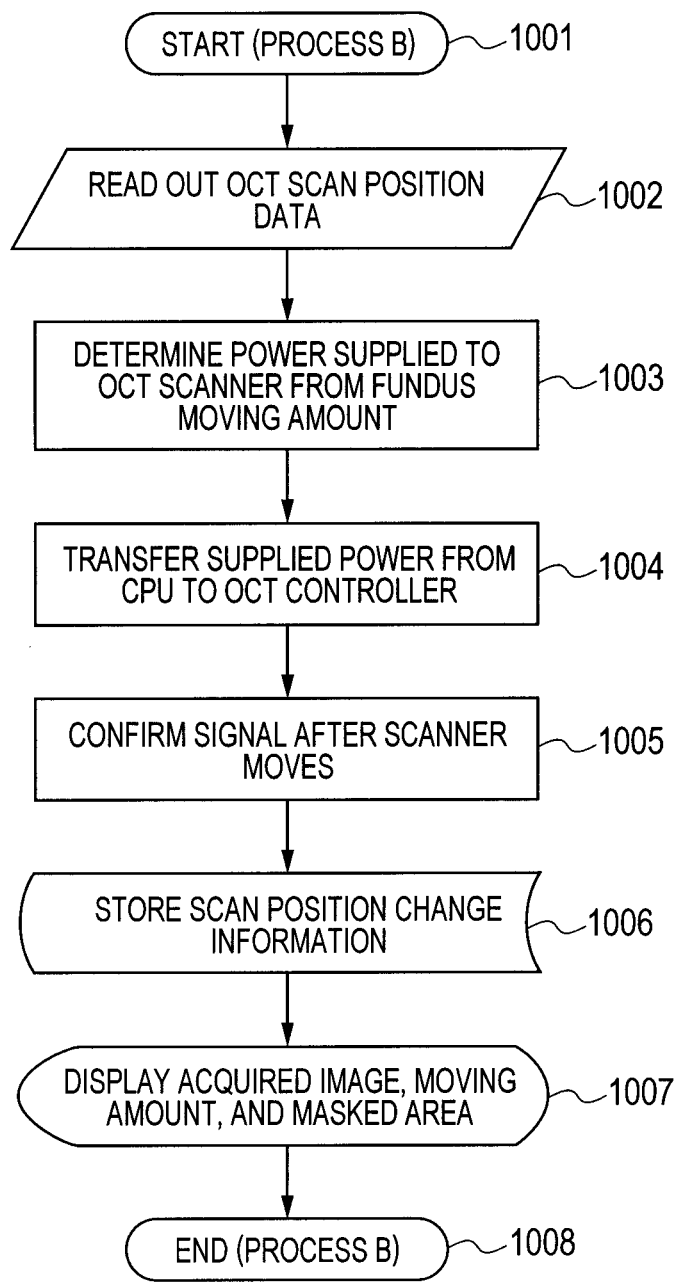
FIG. 10 is a schematic diagram of process B according to the first embodiment of the present invention.

Process B will be described with reference to FIG. 10. OCT scan position is read out (step 1002), power to be supplied to the OCT scanners is determined based on the moving amount ($\Delta x$, $\Delta y$) of the fundus (step 1003), the supplied power is transferred from the CPU to the OCT controller (step 1004), and the X and Y OCT scanners are driven (step 1005). The OCT scan position is recorded (step 1006) and various information is displayed on the display (step 1007).

Figure 11:
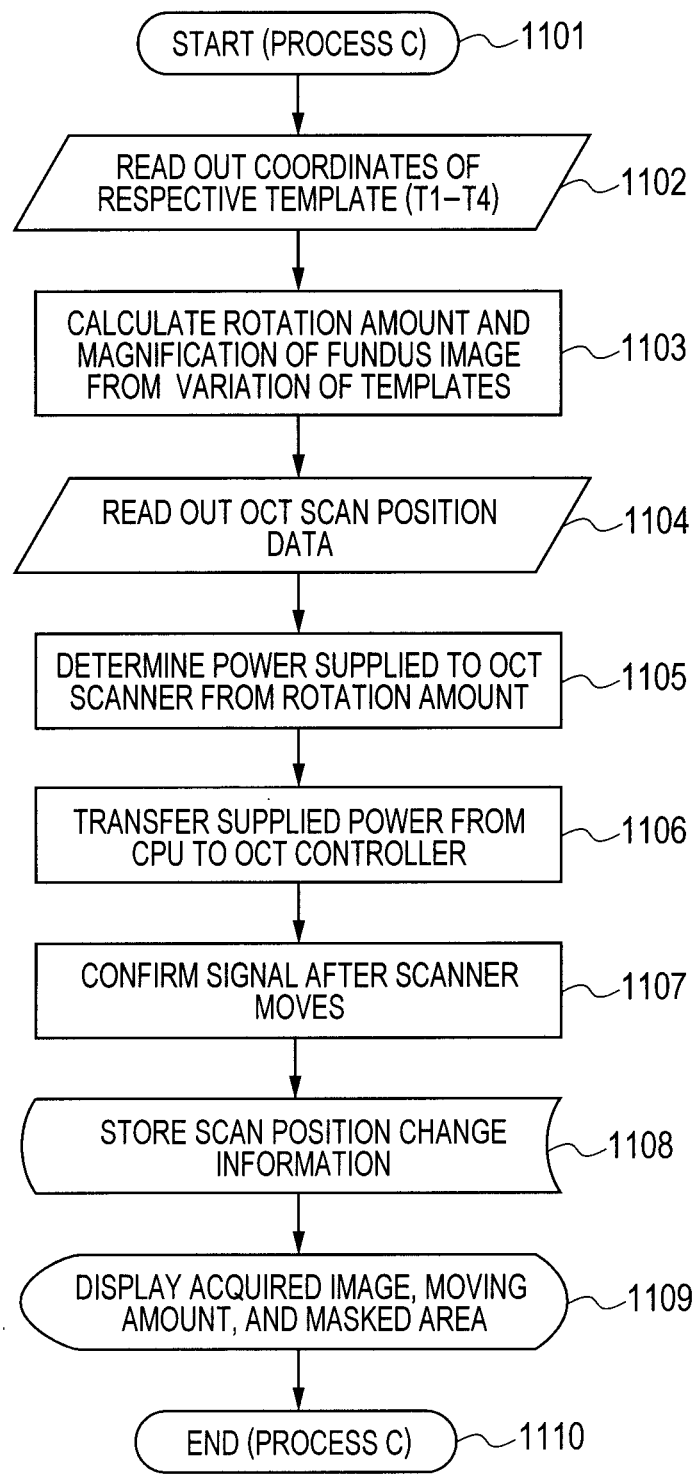
FIG. 11 is a schematic diagram of process C according to the first embodiment of the present invention.

Process C will be described with reference to FIG. 11. The coordinates of templates are read out (step 1102), affine transformations are applied to the coordinates, and thereby rotation amounts and magnification changes of the fundus are calculated (step 1103). Furthermore, position data of the OCT scanners is read out (step 1104) and the power to be supplied to the OCT scanners is determined based on the rotation amounts (step 1105). The supplied power is transferred from the CPU to the OCT controller (step 1106), it is confirmed that the scanners have moved (step 1107), and the various information is saved (step 1108) and displayed (step 1109).

(Concrete Example)

Using the apparatus described above, the OCT imaging unit acquires 6×2 mm (x, z) images at 60 Hz and the SLO imaging unit acquires 8×6 mm (x, y) images at 20 Hz.

Figure 3:
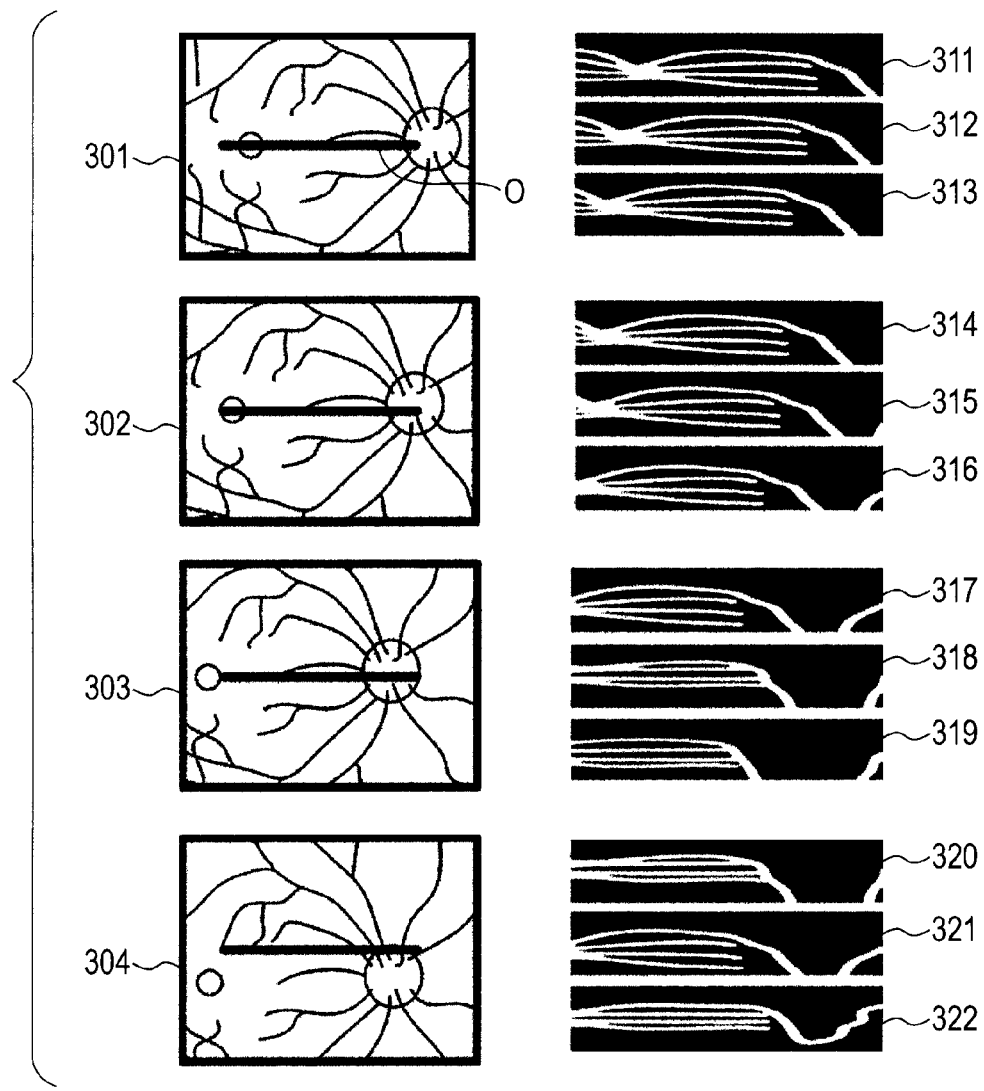
FIG. 3 is a schematic diagram of SLO images and OCT images according to a conventional example in the present invention.

Hereinafter, a direction along the optic axis will be designated as a z direction, a direction parallel to the fundus plane will be designated as an x direction, and a direction vertical to the fundus plane will be designated as a y direction. Images acquired by the two imaging units are shown in FIG. 3. The OCT imaging unit and SLO imaging unit are controlled by the same CPU. Three OCT images are acquired while one SLO image is acquired.

Figure 4:
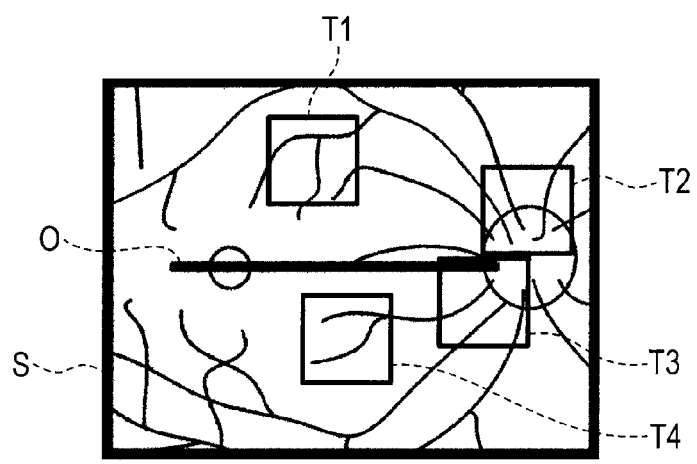
FIG. 4 is a schematic diagram of a fundus image and templates according to the first embodiment of the present invention.

As shown in FIG. 4, an SLO image is acquired and four templates T1, T2, T3 and T4 are extracted from the SLO image as feature points. According to the present embodiment, intersections of blood vessels are extracted as feature points. The extracted template information is recorded in the recording unit 207. The template information includes coordinate position corresponding to an origin of the SLO image (e.g., scan start position or center position), size, and image information (feature value). Then, an OCT image covering a range (indicated by a thick line O) from the macula to an edge of the optic disk in the SLO image is acquired.

Figure 5:
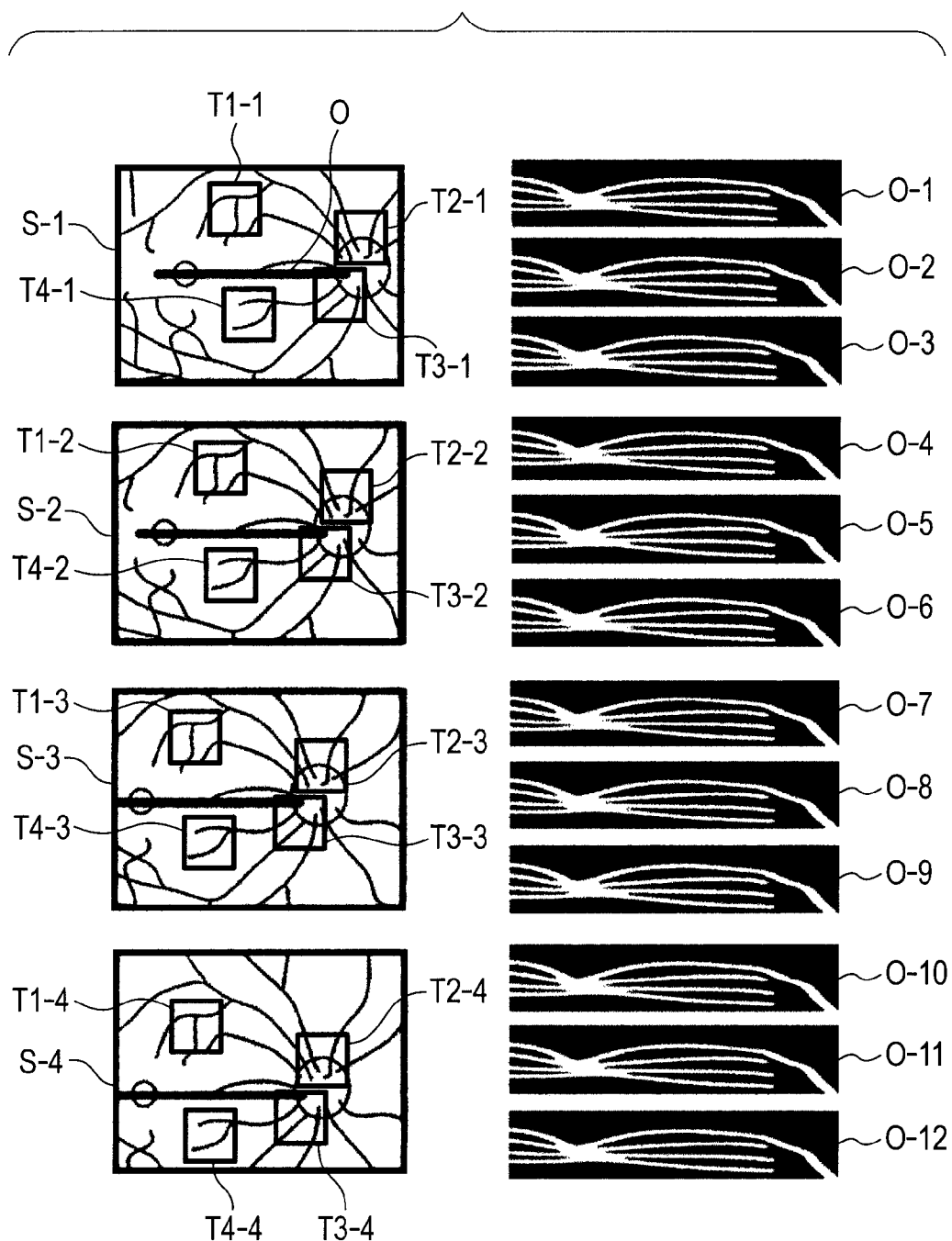
FIG. 5 is a schematic diagram of SLO images and OCT images according to the first embodiment of the present invention.

Next, tracking control will be described with reference to FIGS. 4 and 5. The SLO beam is scanned by operating the SLO imaging unit at the instant when the OCT imaging unit starts imaging. Consequently, while acquiring an SLO image S-1, T1-1 which corresponds to the template T1 closest to scan start position is acquired from part of the SLO image S-1. The moving amount (Δx, Δy) of the fundus is calculated from a difference between T1 coordinates of the initial SLO image S and T1-1 coordinates of the image S-1. The calculated moving amount is fed back to the X and Y scanners of the OCT imaging unit in real time. The feedback allows the OCT beam to scan the same location in the fundus. Similar control is performed for the templates T2 to T4 in order of increasing distance from the scan start position. Even during acquisition of the SLO image, feedback at an average of approximately 80 Hz allows the OCT imaging unit to scan a desired position. After the entire SLO image S-1 is acquired, Δx, Δy, rotation and magnification are calculated by applying affine transformations to T1 to T4 of the SLO image S and T1-1 to T4-1 of the SLO image S-1, and results are reflected in the galvano scanners of the OCT imaging unit, allowing corrections to be made even to parameters other than the shift amounts. The above process is also applied to SLO images S-2 to S-4 in sequence. Regarding the scan position, the OCT imaging unit can scan the same position in the fundus and thereby acquire OCT images at the same position as is the case with O-1 to O-12 in FIG. 5.

That is, according to the present invention, a plurality of fundus images (S, S1, and S2 to S4) of the subject's eye is acquired at different times, a plurality of characteristic images (T1-1 to T4-1) is extracted from each of the fundus images, and the movements of the subject's eye are measured based on the extracted characteristic images. Therefore, the fundus image acquisition unit acquires a plurality of fundus images. Also, the scanning unit according to the present invention scans the subject's eye with measuring light to acquire tomographic images of the subject's eye. The measuring unit measures the movements of the subject's eye by executing matching of characteristic images extracted from each of the fundus images acquired at different times as described above and the control unit controls the scanning unit according to the movements of the subject's eye found as measurement results. Also, the measuring unit measures the movements of the subject's eye while the plurality of fundus images is being acquired at different times.

Incidentally, the pattern matching using the template T1 may be started when an SLO image for one scan is acquired or when that part of an SLO image which includes the coordinates of the stored template T1 is acquired.

The scanners of the OCT imaging unit makes corrections according to movements of the fundus, but the scanners of the SLO imaging unit do not make corrections according to movements.

That is, according to the present invention, a fundus image is acquired by the SLO imaging unit, a plurality of feature points is extracted from the fundus image, and pattern matching is performed by extracting feature points from another SLO image. Furthermore, when movements are measured in relation to one feature point, the subject's eye is scanned with measuring light to acquire a tomographic image.

As described above, a plurality of tomographic images can be acquired at the same position by scanning the same location of the fundus with the OCT beam. Also, the plurality of fundus tomographic images thus acquired can be superimposed to enable observation of minute blood vessels, their abnormalities, edema, tumors or treatment scars, without using image processing to align the images.

Although in the present embodiment, tracking control is performed by extracting templates from four locations, similar effects can be obtained if templates are extracted from two or more locations.

Also, in the present invention, the start of a template matching process is controlled based on positional information about a plurality of feature points extracted from a fundus image.

Second Embodiment

The present embodiment includes an internal fixation lamp, an SLO imaging unit, and an OCT imaging unit and involves comparing an acquisition rate of fundus tomographic images by the OCT imaging unit and an acquisition rate of SLO images by the SLO imaging unit, determining the number of templates to be extracted from each SLO image according to the acquisition rate of OCT images, correcting acquisition position of the next OCT image based on each template, thereby linking tracking speed and imaging speed of the OCT imaging unit to each other, and thereby performing optimal tracking. The apparatus configuration is the same as the first embodiment, and thus description thereof will be omitted.

Figure 6:
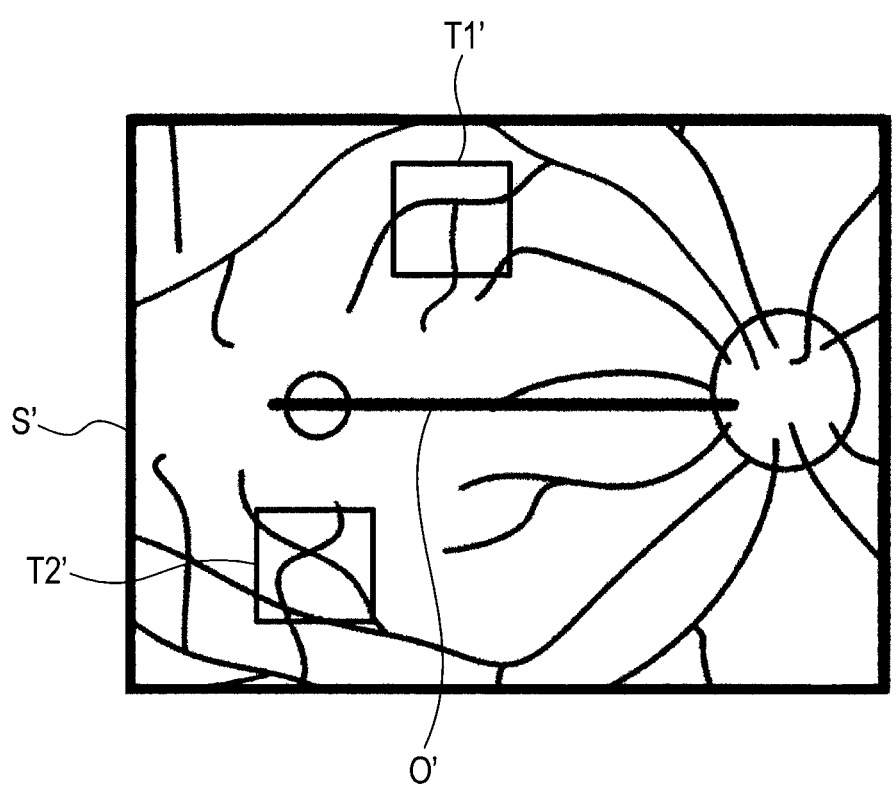
FIG. 6 is a schematic diagram of a fundus image and templates according to a second embodiment of the present invention.

According to the present embodiment, the OCT imaging unit acquires 6×2 mm images at 40 Hz and the SLO imaging unit acquires 8×6 mm images at 20 Hz. While the SLO imaging unit acquires one SLO image, two OCT images can be acquired, and thus templates, i.e., feature points, are extracted from two locations. An extracted image is shown in FIG. 6. Templates T1' and T2' are extracted from the acquired SLO image S' and the extracted template information is recorded in the recording unit 207. An OCT imaging area O' corresponds to a scan range from the macula to an edge of the optic disk.

Figure 7:
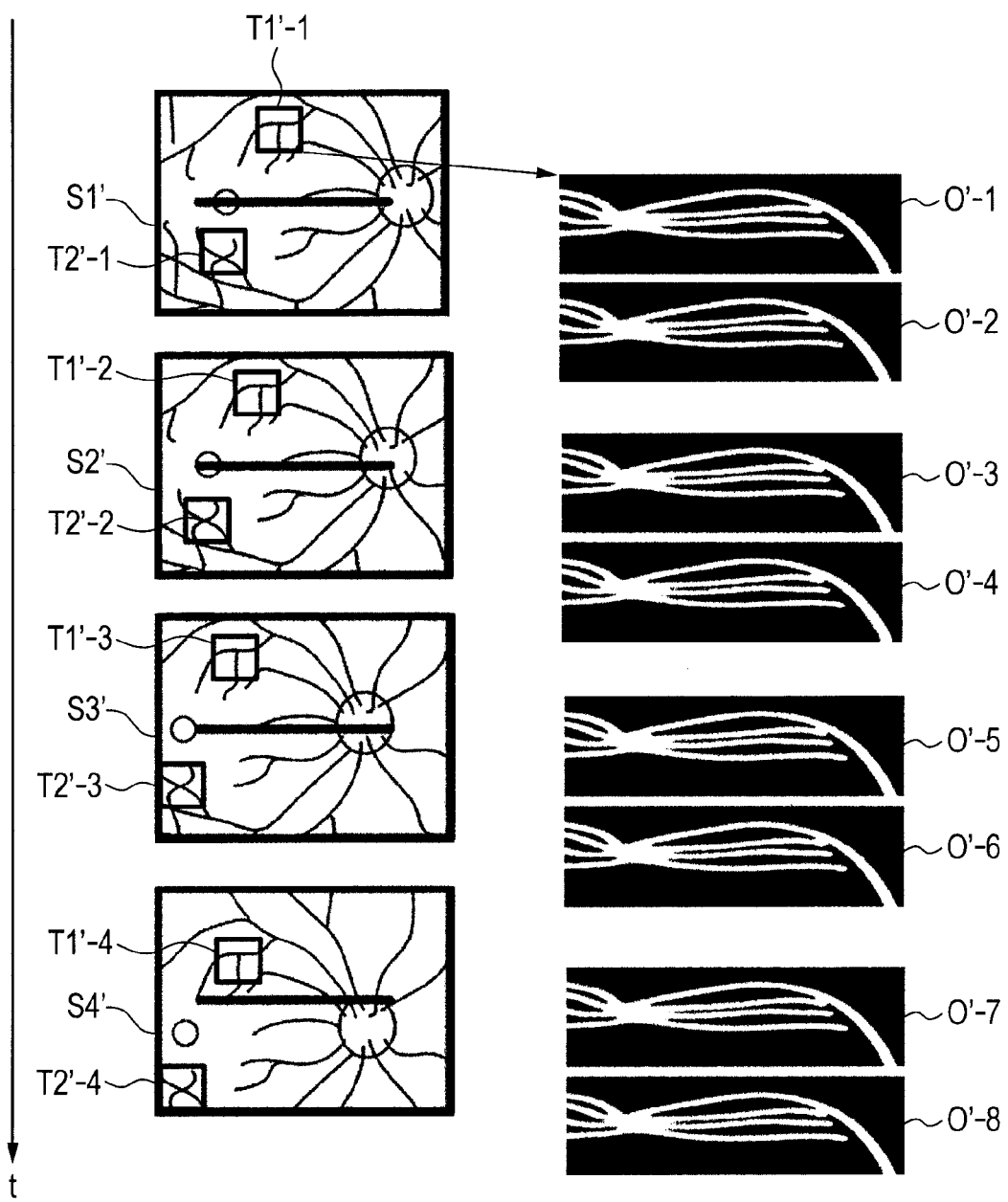
FIG. 7 is a schematic diagram of SLO images and OCT images according to the second embodiment of the present invention.

Before imaging is started by the OCT imaging unit, while part of an image S1' is being acquired, a location which corresponds to the templates T1' extracted from the SLO image S' is searched for as shown in FIGS. 6 and 7. When T1'-1 which corresponds to the template T1' is acquired from part of the SLO image S1', the moving amount (Δx, Δy) of the fundus is calculated from a difference between T1' coordinates of the initial SLO image S' and T1'-1 coordinates of the image S1'. The calculated moving amount is fed back to the X and Y scanners of the OCT imaging unit in real time. Simultaneously with the feedback, an OCT image is captured by the OCT imaging unit. Similar control is performed for the template T2'. Even during acquisition of the SLO image, if the acquisition of the SLO image is synchronized with the OCT image by means of real-time feedback, a desired position can be scanned with the OCT beam at about 40 Hz on a template by template basis. The control described above allows calculation results to be used in capturing each OCT image, and an OCT image O'-1 corresponding to the template T1'-1 and an OCT image O'-2 corresponding to the template T2'-1 are acquired as shown in FIG. 7. Once the entire SLO image S1' is captured, the rotation amount of the fundus is calculated from the SLO image S1' and templates of the SLO image S1'. The calculated rotation amount is fed back to the OCT galvano scanners.

A similar process is performed for SLO images S2' to S4', allowing tracking to be performed at about 40 Hz in synchronization with the image acquisition rate of the OCT imaging unit.

As described above, a plurality of tomographic images can be acquired at the same position by scanning the same location of the fundus with the OCT beam. Also, the plurality of fundus tomographic images can be superimposed to enable observation of minute blood vessels, edema, or tumors, without using image processing to align the images. Incidentally, in the present embodiment, after the movements of the subject's eye are measured, the rotation amount of the fundus or rotation amount of the subject's eye is measured by the measuring unit, but the magnification of the subject's eye rather than the rotation amount may be found by a similar technique. Alternatively, both rotation amount and magnification may be found.

In the present embodiment, templates are extracted at two locations because the acquisition rate of OCT images is twice as high as the acquisition rate of SLO images, and templates can be extracted from as many locations as the ratio of the acquisition rates.

That is, preferably the acquisition rate of OCT images is an integral multiple of the acquisition rate of SLO images, and thus the number of feature points extracted initially is preferably set equal to the quotient of the acquisition rate of the OCT images divided by the acquisition rate of the SLO images.

Other Embodiments

Although an internal fixation lamp is used in the first and second embodiments, an external fixation lamp may be used alternatively. When an external fixation lamp is used, ocular fixation becomes less stable than when an internal fixation lamp is used.

Also, the fundus photographing apparatus may be an LSLO (Line Scanning Laser Ophthalmoscope) instead of an SLO. In that case, needless to say, the SLO scanner (X) becomes unnecessary.

Furthermore, although in the above embodiments, positional information is reflected in real time, the positional information may be reflected after the acquisition of an SLO image.

If templates are detected at more than two locations, rotation and magnification may be calculated by affine transformations or the like even during acquisition of the same fundus image and fed tack to the OCT apparatus.

The present invention can also be implemented by software (program) which implements the functions of the above embodiments if the software (program) is supplied to a system or apparatus via a network or any of various storage media and a computer (or a CPU or MPU) of the system or apparatus then reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-052290, filed Mar. 10, 2011, which is hereby incorporated by reference herein in its entirety.

What is claimed is:

1. An ophthalmologic apparatus, which measures movements of an eye, the apparatus comprising:
   a first optical scanning unit configured to scan first measuring light in a first scanning area of the eye;
   a second optical scanning unit configured to scan second measuring light in a second scanning area of the eye, the second scanning area being larger than the first scanning area;
   a fundus image acquisition unit configured to acquire, using the second optical scanning unit, a plurality of fundus images of the eye at different times, wherein each fundus image of the plurality of fundus images includes different partial areas being acquired in turn, and wherein an acquisition rate of first images of the eye acquired using the first optical scanning unit is faster than an acquisition rate of the plurality of fundus images;
   a selecting unit configured to select, in each area of a plurality of areas acquired in turn in a fundus image of the plurality of fundus images, respectively different partial areas in turn;
   a measuring unit configured to, for the fundus image of the plurality of fundus images, measure, using (a) in turn the selected different partial areas of the fundus image and (b) another fundus image of the plurality of fundus images, a plurality of movements of the eye so as to obtain, for the fundus image, a plurality of measured movements of the eye; and
   a control unit configured to control the first optical scanning unit to correct, using the plurality of measured movements in turn, a position scanned by the first measuring light.

2. An ophthalmologic apparatus according to claim 1, wherein the fundus image acquisition unit acquires the plurality of fundus images by using a SLO.

3. An ophthalmologic apparatus according to claim 1, wherein the fundus image acquisition unit acquires the plurality of fundus images by using a LSLO.

4. A control method for an ophthalmologic apparatus including a first optical scanning unit configured to scan first measuring light in a first scanning area of an eye to acquire first images of the eye, which measures movements of the eye, the control method comprising steps of:
   acquiring, using a second optical scanning unit configured to scan second measuring light in a second scanning area of the eye, a plurality of fundus images of the eye at different times, the second scanning area being larger than the first scanning area, wherein each fundus image of the plurality of fundus images includes different partial areas being acquired in turn, and wherein an acquisition rate of the first images is faster than an acquisition rate of the plurality of fundus images;
   selecting, in each area of a plurality of areas acquired in turn in a fundus image of the plurality of fundus images, respectively different partial areas in turn;
   for the fundus image of the plurality of fundus images, measuring, using (a) in turn the selected different partial areas of the fundus image and (b) another fundus image of the plurality of fundus images, a plurality of movements of the eye so as to obtain, for the fundus image, a plurality of measured movements of the eye; and controlling the first optical scanning unit to correct, using the plurality of measured movements in turn, a position scanned by the first measuring light.

5. A control method according to claim 4, wherein the plurality of fundus images are acquired by using a SLO.

6. A control method according to claim 4, wherein the plurality of fundus images are acquired by using a LSLO.

7. A non-transitory computer-readable storage medium storing a program for causing a computer to execute the method according to claim 4.

8. An ophthalmologic apparatus according to claim 1, further comprising:

a comparing unit configured to compare an image of each of the different partial areas with the another fundus image, wherein the measuring unit is configured to measure each movement of the plurality of movements using the comparing result of the comparing unit.

9. A control method according to claim 4, further comprising the steps of:

comparing an image of each of the different partial areas with the another fundus image, wherein each movement of the plurality of movements is measured using the comparing result.

10. A non-transitory computer-readable storage medium storing a program for causing a computer to execute the method according to claim 9.

11. An ophthalmologic apparatus according to claim 1, wherein the fundus image acquisition unit is configured to acquire an image of each of the different partial areas, which are a part of the second scanning area, by using return light from the fundus before completing scanning one frame of the second scanning area, during a time in which the second optical scanning unit scans the second measuring light in the second scanning area, and wherein the measuring unit is configured to measure the plurality of movements using the acquired images of the different partial areas and at least a fundus image acquired by scanning the second measuring light in the second scanning area by the second optical scanning unit before starting the scanning the one frame of the second scanning area.

12. A control method according to claim 4, wherein an image of each of the different partial areas, which are a part of the second scanning area, by using return light from the fundus is acquired before completing scanning one frame of the second scanning area, during a time in which the second optical scanning unit scans the second measuring light in the second scanning area, and wherein the measuring measures the plurality of movements using the acquired images of the different partial areas and at least a fundus image acquired by scanning the second measuring light in the second scanning area by the second optical scanning unit before starting the scanning the one frame of the second scanning area.

13. A non-transitory computer-readable storage medium storing a program for causing a computer to execute the method according to claim 12.

14. An ophthalmologic apparatus according to claim 1, wherein the control unit is further configured to, after performing the correction using the plurality of measured movements in turn, control the first optical scanning unit to correct, in accordance with a calculation using the plurality of measured movements, a position scanned by the first measuring light.

15. A control method according to claim 4, further comprising, after the controlling step, a second controlling step of controlling the first optical scanning unit to correct, in accordance with a calculation using the plurality of measured movements, a position scanned by the first measuring light.

16. An ophthalmologic apparatus according to claim 1, wherein the different partial areas are selected in accordance with detection in the fundus image of respective intersections of blood vessels.

17. A control method according to claim 4, wherein the different partial areas are selected in accordance with detection in the fundus image of respective intersections of blood vessels.

18. An ophthalmologic apparatus according to claim 1, wherein the different partial areas are selected in accordance with detection in the fundus image of respectively corresponding features of the eye.

19. A control method according to claim 4, wherein the different partial areas are selected in accordance with detection in the fundus image of respectively corresponding features of the eye.

* * * * *